United States Patent [19]

Speakman et al.

[11] Patent Number: 4,983,587
[45] Date of Patent: Jan. 8, 1991

[54] DIHYDRODIBENZOFURAN DERIVATIVES AND FUNGICIDES CONTAINING THESE COMPOUNDS

[75] Inventors: John-Bryan Speakman, Mannheim; Rudolf Karl, Limburgerhof; Gisela Lorenz, Neustadt; Eberhard Ammermann, Ludwigshafen; Bruno Wuerzer, Otterstadt; Norbert Meyer, Ladenburg; Klaus Ditrich, Bad Durkheim, all of Fed. Rep. of Germany

[73] Assignee: BASF Aktiengesellschaft, Ludwigshafen, Fed. Rep. of Germany

[21] Appl. No.: 379,198

[22] Filed: Jul. 13, 1989

[30] Foreign Application Priority Data

Jul. 29, 1988 [DE] Fed. Rep. of Germany ....... 3825840

[51] Int. Cl.$^5$ ............................................ C07D 307/91
[52] U.S. Cl. ..................................... 514/63; 514/468; 435/126; 549/214; 549/461
[58] Field of Search ................ 549/461, 214; 514/468, 514/63; 435/126

[56] References Cited

U.S. PATENT DOCUMENTS 4,376,776 3/1983 Rentzea et al. .................... 549/460
4,604,128 7/1986 Watson et al. ......................... 71/88

FOREIGN PATENT DOCUMENTS 0057362 1/1982 European Pat. Off. .
0177222 9/1985 European Pat. Off. .
2060205 12/1970 Fed. Rep. of Germany .
1329848 12/1970 United Kingdom .

OTHER PUBLICATIONS

Hermann ROMPP, Chemie Lexikon, 1966, pp. 6820–6821.

Primary Examiner—Mary C. Lee
Assistant Examiner—Bernard L. Dentz
Attorney, Agent, or Firm—Oblon, Spivak, McClelland, Maier & Neustadt

[57] ABSTRACT

Substituted benzofuran derivatives of the formula

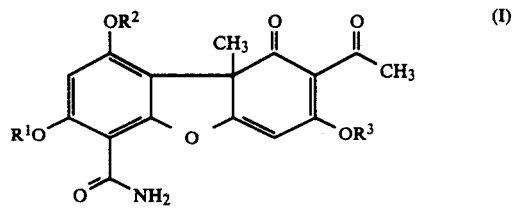

where $R^1$, $R^2$ and $R^3$ are hydrogen, an alkali or alkaline earth metal, alkyl, aralkyl, alkanoyl, halogen-substituted alkanoyl, benzoyl or a radical $R^4R^5R^6Si$ in which $R^4$, $R^5$ and $R^6$ are alkyl, and fungicides containing these compounds.

7 Claims, No Drawings

DIHYDRODIBENZOFURAN DERIVATIVES AND FUNGICIDES CONTAINING THESE COMPOUNDS

The present invention relates to substituted benzofuran derivatives, processes for their preparation and fungicides which contain these compounds as active ingredients.

It is known that usnic acid

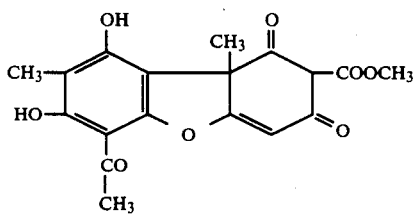

(2,6-diacetyl-7,9-dihydroxy-8,9b-dimethyl-1,3(2H,9bH)-dibenzofurandione) has antibacterial activity (Römpp, Chemie Lexikon, 1966, pages 6820 and 6821).

We have found that novel substituted benzofuran derivatives of the formula I

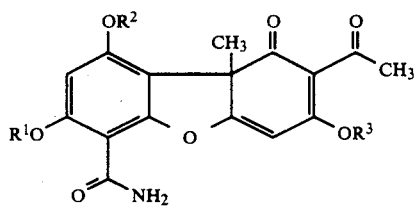

where $R^1$, $R^2$ and $R^3$ are identical or different and are each hydrogen, an alkali or alkaline earth metal, unsubstituted or substituted $C_1$–$C_4$-alkyl, $C_2$–$C_4$-alkanoyl, halogen-substituted $C_2$-alkanoyl, unsubstituted or substituted aralkyl, unsubstituted or substituted benzoyl or a radical $R^4R^5R^6Si$ in which $R^4$, $R^5$ and $R^6$ are identical or different and are each $C_1$–$C_6$-alkyl, have a fungicidal action which is better than that of usnic acid.

In formula I, $R^1$, $R^2$ and $R^3$ may be an alkali or alkaline earth metal, e.g. Na, Mg or Ca, $C_1$–$C_4$-alkyl, e.g. methyl, ethyl or n-butyl, $C_2$–$C_4$-alkanoyl, e.g. acetyl, propionyl or butyryl, a halogen-substituted alkanoyl radical, e.g. trifluoroacetyl, a $C_7$–$C_9$-phenylalkyl or benzoyl radical which is unsubstituted or substituted by halogen or $C_1$–$C_4$-alkyl, for example benzyl, phenylethyl, p-chlorobenzyl, m-chlorobenzyl or p-methylbenzyl, or a radical of the formula $R^4R^5R^6Si$, in which $R^4$, $R^5$ and $R^6$ are identical or different and are each $C_1$–$C_4$-alkyl, e.g. methyl, ethyl or n-butyl.

The derivatives of the formula I, where $R^1$ to $R^3$ are each $C_1$–$C_4$-alkyl or unsubstituted or substituted aralkyl, are obtained, for example, by reacting a compound of the formula I, in which one or more of the radicals $R^1$, $R^2$ and $R^3$ is hydrogen, with an alkylating agent of the formula $$R^7\text{—}X \qquad (II)$$

where $R^7$ has the abovementioned meanings of $R^1$, $R^2$ and $R^3$, except hydrogen, and X is halogen or $OSO_2R^7$, in the presence of an inert solvent and in the presence or absence of a base. The reaction takes place at, for example, from 20° to 100° C., preferably from 40° to 80° C.

Derivatives of the formula I where $R^1$ to $R^3$ are identical or different and are each $C_2$–$C_4$-alkanoyl, halogen-substituted $C_2$-alkanoyl or unsubstituted or substituted benzoyl can be prepared, for example, by reacting a compound of the formula I, in which one or more of the radicals $R^1$, $R^2$ and $R^3$ is hydrogen, with an anhydride of the formula

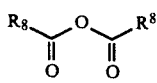

where $R^8$ is $C_1$–$C_3$-alkyl, e.g. methyl, ethyl or propyl, halogen-substituted $C_1$-alkyl, e.g. trifluoromethyl, or unsubstituted or substituted phenyl, e.g. chlorophenyl, tolyl or methoxyphenyl, in the presence of an inert solvent at from 80° to 120° C., or with an acyl chloride of the formula $$R^8\text{—CO—Cl} \qquad (IV)$$

where $R^8$ has the abovementioned meanings, in the presence or absence of a base at from 20° to 120° C., preferably from 60° to 80° C.

The silylated derivatives of the formula I, in which $R^1$, $R^2$ and $R^3$ are identical or different and are each a radical of the formula $R^4R^5R^6Si$, can be obtained, for example, by reacting a compound of the formula I, in which one or more of the radicals $R^1$, $R^2$ and $R^3$ is hydrogen, with a chlorosilane of the formula

in which $R^4$, $R^5$ and $R^6$ are each $C_1$–$C_6$-alkyl, in the presence of an inert solvent and of a base at from 20° to 70° C., or with a silyl derivative of the formula $R^9CONHSi$-$R^4R^5R^6$, where $R^9$ is methyl or trifluoromethyl and $R^4$, $R^5$ and $R^6$ have the abovementioned meanings, or with a silyl derivative of the formula

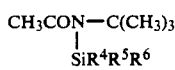

at from 0° to 50° C., preferably from 30° to 40° C.

Suitable silyl derivatives of acetamide, of trifluoroacetamide or of N-tert-butylacetamide are, for example, the trimethylsilyl, triethylsilyl and n-butyldimethylsilyl derivatives.

Suitable solvents for the abovementioned processes are, for example, halohydrocarbons, in particular chlorohydrocarbons, e.g. tetrachloroethylene, 1,1,2,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic, cycloaliphatic and aromatic hydrocarbons, e.g. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,3,3-trimethylpentane, 2,3,3-trimethylpentane, octane, toluene, o-, m- and p-xylene and tetralin; esters, e.g. ethyl acetate, ethyl acetoacetate and isobutyl acetate; amides, e.g. formamide, methylformamide and dimethylformamide, ketones, e.g. acetone and methyl ethyl ketone; alcohols, such as methanol, ethanol and isopropanol; sulfoxides, such as dimethyl sulfoxide; heteroaromatics, such as pyridine, $\alpha$-, $\beta$- and $\gamma$-picoline, and pyrimidine, and mixtures of these. Advantageously, the solvent is used in an amount of from 100 to 2,000, preferably from 200 to 700, % by weight, based on the starting material II, III, IV, V or VI.

Suitable bases for the reaction of compounds of the formula I, where one or more of the radicals $R^1$ to $R^3$ is hydrogen, with a compound of the formula II, IV or V are tertiary amines, alkaline earth metal compounds, ammonium compounds and alkali metal compounds and mixtures of these. Zinc compounds may also be used. Examples are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc acetate, zinc formate, sodium acetate, trimethylamine, triethylamine, tripropylamine, triisopropylamine, tributylamine, triisobutylamine, tri-sec-butylamine, tri-tert-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidine, N-ethylpyrrolidine, N-methylpiperidine, N-ethylpiperidine, N-methylpyrrolidone, N-ethylpyrrolidone, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, $\alpha$-picoline, $\beta$-picoline, $\gamma$-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, furfurylamine and triethylenediamine.

In addition to the abovementioned bases, examples of other suitable bases are sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec-butylate, sodium tert-butylate, sodium ethylene glycolate, sodium 1,2-propylene glycolate, sodium 1,3-propylene glycolate, sodium diethylene glycolate, sodium triethylene glycolate, sodium 1,2-dipropylene glycolate, potassium methylate, potassium ethylate, potassium n-propylate, potassium isopropylate, potassium n-butylate, potassium isobutylate, potassium sec-butylate, potassium tert-butylate, potassium methylene glycolate, potassium 1,2-propylene glycolate, potassium 1,3-propylene glycolate, potassium diethylene glycolate, potassium triethylene glycolate and potassium 1,2-dipropylene glycolate.

All the processes may be carried out continuously or batchwise, under atmospheric or superatmospheric pressure; for the sake of simplicity, atmospheric pressure is preferred.

EXAMPLES

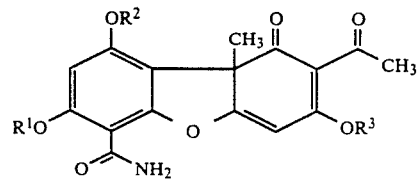

| No. | $R^1$ | $R^2$ | $R^3$ | Bp. |
|---|---|---|---|---|
| 1 | H | H | H | 180–182° C. (decomp.) |
| 2 | $CH_3$ | $CH_3$ | H | |
| 3 | $CH_3CO$ | $CH_3CO$ | H | |
| 4 | $Si(CH_3)_3$ | $Si(CH_3)_3$ | H | |
| 1a | Na salt of No. 1 | | | |
| 1b | Mg salt of No. 1 | | | |
| 1c | Ca salt of No. 1 | | | |
| 8 | H | H | $CH_3$ | |
| 9 | H | H | $Si(CH_3)_3$ | |
| 10 | H | H | $COCH_3$ | |
| 11 | H | H | $COCF_3$ | |
| 12 | $CH_3$ | $CH_3$ | $CH_3$ | |
| 13 | $COCH_3$ | $COCH_3$ | $COCH_3$ | |
| 14 | $Si(CH_3)_3$ | $Si(CH_3)_3$ | $Si(CH_3)_3$ | |

Compound No. 1, 2-acetyl-3,7,9-trihydroxy-6-carboxamido-9b-methyl-1(1H,9bH)-dibenzofuranone, can be prepared, for example, by cultivating the fungus DSM 4431 and separating it off from the culture filtrate.

The fungus DSM 4431 was isolated from a lawn sample (Speyer, FRG). A viable culture of this microorganism has been deposited at the Deutsche Sammlung für Mikroorganismen, Mascheroder Weg 1b, 3300 Braunschweig, and incorporated into its permanent collection. The microorganism is freely accessible to the public at this depositary under its depositary number DSM 4431.

Compound No. 1 is in general prepared by cultivating the fungus DSM 4431 under aerobic conditions in a liquid medium containing assimilable sources of carbon, nitrogen and inorganic anions and cations, until a significant amount of compound no. 1 has formed in the medium, and this compound is then isolated from the said medium.

Compound No. 1 is prepared, for example, by fermenting, under aerobic conditions, a liquid medium which contains assimilable sources of carbon, nitrogen and inorganic anions and cations, the medium having been inoculated with a viable culture of DSM 4431 or with a mutant of the said fungus which produces the compound no. 1, cultivating the organism with sterile aeration and with stirring for from 50 to 150 hours at from 20° to 30° C. and a pH of from 5.5 to 8.0, separating off the culture filtrate and extracting the compound from it.

Compound No. 1 can be obtained, for example, by extracting it from the culture filtrate with a water-immiscible solvent, or by freeze-drying the culture filtrate and then extracting the said compound from it with a solvent.

The extract can be purified, for example, by a chromatographic method.

Not only compound no. 1 but also the fermentation broth or total slurry of the microorganism DSM 4431 is suitable for use as a fungicide.

It is also possible to use the extract obtained from the fermentation broth or total slurry of the microorganism DSM 4431.

Compound No. 1 is formed in the course of the cultivation of the fungus DSM 4431 under controlled conditions.

General Fermentation Conditions

The fungus DSM 4431 can be cultivated in a wide variety of liquid culture media. Suitable nutrient media include an assimilable source of carbon, such as dextrin, sucrose, molasses, glycerol, etc., an assimilable source of nitrogen, such as protein, protein hydrolysis products, polypeptides, amino acid, corn steep liquor, etc., and an assimilable source of organic anions and cations, such as potassium, sodium, ammonium, calcium, sulfate, carbonate, phosphate, chloride, etc. Trace elements, such as boron, molybdenum, copper, manganese, zinc, iron, etc., are introduced into the media in the form of impurities of the other constituents of the media or as defined solutions. Aeration in bottles and tanks is effected by passing sterile air through the nutrient medium or forcing it onto the surface of the nutrient medium. Further agitation in the tanks is ensured by means of a mechanical stirrer. If necessary, an anti-foam, such as silicone oil, may be added.

EXAMPLE a

Preparation of the Inoculum

Suitable media as used for the cultivation of the inoculum are malt extract (2%) or sugar beet molasses (2%).

(aa) For fermentation on a small scale

The nutrient media are sterilized. The agar (2% malt extract), which is uniformly covered with a growth of the germ-free culture of the fungus DSM 4431 and is present in a glass dish of 9 cm diameter, is homogenized in a sterilized mixer with the addition of 200 ml of sterilized (demineralized) water, and 40 ml portions of this homogenized material are used as an inoculum for culturing the fungus in glass flasks (500 ml of nutrient medium in each case).

(ab) For fermentation on a larger scale

The nutrient media are sterilized. The agar (2% malt extract), which is uniformly covered with a growth of the germ-free culture of the fungus DSM 4431 and obtained from 5 glass dishes of 9 cm diameter, is homogenized in a sterilized mixer with the addition of 400 ml of sterilized (demineralized) water, after which half of this homogenized material is transferred, as an inoculum, to 1 l glass flasks (with 500 ml of nutrient medium in each case). The media are then shaken for from 24 to 30 hours at 25° C. on a rotary shaking machine (130–150 rpm). This inoculum is then used to inoculate 15 l of a sterile sugar beet molasses medium (2%).

EXAMPLE b

Fermentation on a Small Scale

To prepare the fermentation media, sugar beet molasses (2%) was used. After inoculation of the sterilized media (500 ml of nutrient medium per flask) with the inoculum prepared according to Example aa, the media were then shaken for from 5 to 6 days at 25° C. on a rotary shaking machine (130–150 rpm), after which the slurry was harvested.

EXAMPLE c

Fermentation on a Larger Scale

To prepare the fermentation media, sugar beet molasses (2%) was used. After inoculation of the sterilized media (15 l of nutrient medium in each case) with the inoculum prepared according to Example ab, the fermentation is carried out at 25° C., a sterile air stream of from 1.5 to 2 l/min being maintained, and with stirring with a paddle stirrer operated at 150 rpm. The fermentation is effected for from 5 to 8 days, after which the slurry is harvested.

Fermentations on a 50 l, 100 l and 2,000 l scale are carried out similarly to this Example, the amount of inoculum and the sterile air stream being adapted to the changed volumes of nutrient medium.

EXAMPLE d

Isolation of Compound No. 1

A total volume of about 8 liters of slurry, prepared according to Example b or c, is filtered, and the mycelium cake is discarded. The culture filtrate thus obtained is extracted with dichloromethane in a continuous extraction process, and the solvent is then removed from this extract in a rotary evaporator under reduced pressure. The residue is taken up in a small volume of a 60:35:5 mixture of dichloromethane/dioxane/methanol, and the solution is applied to a column, previously equilibrated with the mobile phase, and is chromatographed under pressure.

Conditions:
Column:
  Internal diameter 5.4 cm
  Height of packing 60.0 cm
Stationary phase:
  Silica 25–40 μm
  (Merck LichroPrep Si 60)
Mobile phase:
  Dichloromethane:dioxane:methanol = 60:35:5
Flow rate:
  45 ml/min
Pressure:
  1 bar
Detection of the eluate by means of a photometer:
  $\lambda = 254$ or 260 nm.

The fraction containing the major part of the biologically active substance is evaporated to dryness in a rotary evaporator under reduced pressure and the residue is then taken up in a little methanol. The active compound can be crystallized out by adding water, and a very pure substance is obtained by repeated recrystallization. The compound thus obtained is partially in the form of a Ca or Mg salt, and the proportions of Ca and Mg can obviously vary to a greater or lesser extent depending on the culture conditions for the microorganism. Compound No. 1 is obtained by dissolving appropriate amounts of the starting compound isolated from the culture filtrate in 2% strength sulfuric acid with the addition of acetone (because of the low solubility of the compound in water), stirring for 2 hours at room temperature (20° C.) and then extracting with $CH_2Cl_2$. The $CH_2Cl_2$ phase is evaporated down in a rotary evaporator under reduced pressure, after which the residue is taken up in methanol and the product is crystallized out with the addition of water. The pure compound no. 1 is obtained by repeated recrystallization.

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Uncinula necator in vines,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1 is dissolved in a mixture consisting of 40 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
3 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The prior art usnic acids (dextrorotatory and levorotatory) were used as comparative active ingredients.

USE EXAMPLE 1

Action on *Botrytis cinerea* in Pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus *Botrytis cinerea* and kept in a high-humidity chamber at 22° to 24° C. After 5 days, the disease had spread on the untreated control plants to such an extent that the necroses covered the major portion of the leaves.

| Active ingredient | Leaf attack in % after application of a 0.05% aqueous active ingredient formulation |
|---|---|
| 1 | 3 |
| Usnic acid (+) | 40 |
| Usnic acid (−) | 40 |
| Untreated | 100 |

USE EXAMPLE 2

Action on *Pyrenophora teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

| Active ingredient | Leaf attack in % after application of a 0.05% aqueous active ingredient formulation |
|---|---|
| 1 | 10 |
| Usnic acid (+) | 20 |
| Usnic acid (−) | 20 |
| Untreated | 100 |

We claim:

1. Substituted benzofuran derivatives having fungicidal properties of the formula I

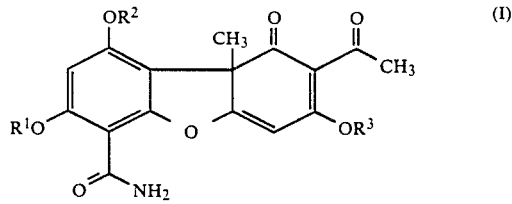

where $R^1$, $R^2$ and $R^3$ are identical or different and are each hydrogen, an alkali or alkaline earth metal, unsubstituted or substituted $C_1$–$C_4$-alkyl, unsubstituted or substituted aralkyl, $C_2$–$C_4$-alkanoyl, halogen-substituted $C_2$-alkanoyl, unsubstituted or substituted benzoyl or a radical $R^4R^5R^6Si$ in which $R^4$, $R^5$ and $R^6$ are identical or different and are each $C_1$–$C_4$-alkyl.

2. Substituted benzofuran derivatives of the formula I as set forth in claim 1, where $R^1$, $R^2$ and $R^3$ are identical or different and are each hydrogen or an alkali metal or alkaline earth metal.

3. A method of combatting fungi, wherein the fungi or the seeds, plants, materials or the soil to be protected against fungus attack are treated with a fungicidally effective amount of the fermentation broth or total slurry of the microorganism DSM 4431.

4. A process for the manufacture of benzofuran derivatives of the formula I as set forth in claim 1, where $R^1$, $R^2$ and $R^3$ are each hydrogen, wherein the fungus DSM 4431, or a mutant thereof producing said benzofuran derivatives, is fermented under aerobic conditions in a liquid medium containing assimilable sources of carbon, nitrogen and inorganic anions and cations, until a significant amount of the benzofuran derivative has formed in the medium, and the benzofuran derivative is isolated from the medium.

5. A fungicide containing an inert additive and a fungicidally effective amount of a substituted benzofuran derivative of the formula I

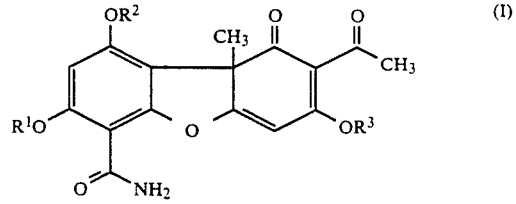

where $R^1$, $R^2$ and $R^3$ are identical or different and are each hydrogen, an alkali or alkaline earth metal, unsubstituted or substituted $C_1$–$C_4$-alkyl, unsubstituted or substituted aralkyl, $C_2$–$C_4$-alkanoyl, halogen-substituted $C_2$-alkanoyl, unsubstituted or substituted benzoyl or a radical $R^4R^5R^6Si$ in which $R^4$, $R^5$ and $R^6$ are identical or different and are each $C_1$–$C_4$-alkyl.

6. A process for combating fungi, wherein the fungi or the seeds, plants, materials or soil to be protected against fungus attack are treated with a fungicidally effective amount of a substituted benzofuran derivative of the formula I

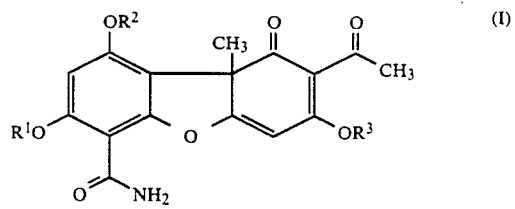

where $R^1$, $R^2$ and $R^3$ are identical or different and are each hydrogen, an alkali or alkaline earth metal, unsubstituted or substituted $C_1$–$C_4$-alkyl, unsubstituted or substituted aralkyl, $C_2$–$C_4$-alkanoyl, halogen-substituted $C_2$-alkanoyl, unsubstituted or substituted benzoyl or a radical $R^4R^5R^6Si$ in which $R^4$, $R^5$ and $R^6$ are identical or different and are each $C_1$–$C_4$-alkyl.

7. A compound of the formula I as set forth in claim 1, where $R^1$, $R^2$ and $R^3$ are each hydrogen.

* * * * *